United States Patent Office

Re. 27,606
Reissued Apr. 3, 1973

27,606
ALUMINUM PLATING PROCESS

Donald L. Schmidt, 2412 St. Marys Drive, Midland, Mich. 48640, and Reinhold Hellmann, 30526 Bluehill, Roseville, Mich. 48066

No Drawing. Original No. 3,462,288, dated Aug. 19, 1969, Ser. No. 558,583, June 20, 1966. Application for reissue Aug. 16, 1971, Ser. No. 172,331
Int. Cl. C23c *3/00*
U.S. Cl. 117—37 56 Claims

Matter enclosed in heavy brackets [ ] appears in the original patent but forms no part of this reissue specification; matter printed in italics indicates the additions made by reissue.

ABSTRACT OF THE DISCLOSURE

Aluminum is plated on a substrate by contacting the substrate with aluminum hydride and a decomposition catalyst. The decomposition catalyst is a compound of a metal of Group IVb or Vb of the Periodic Table or mixtures thereof.

This invention relates to a non-electrolytic process for the plating of aluminum on various substrates and more particularly relates to a relatively low temperature process for the plating of metallic aluminum from an aluminum hydride.

It is known that metallic aluminum may be plated from aluminum hydrides by contacting such hydrides with a substrate at or above the decomposition temperature of the aluminum hydride. Such a process usually requires a relatively high temperature to cause decomposition of the aluminum hydride and therefore cannot be used to plate aluminum onto many heat sensitive substrates. It would be highly desirable, therefore, to have a process which would permit the plating of aluminum at relatively low temperatures.

Likewise, it is known that plating processes are general in nature and cause plating over the entire exposed surface of the substrate and it would be highly desirable to be able to plate only selected areas of a substrate in order to produce patterns or lettering. In addition, most known aluminum plating processes do not give a coating of uniform thickness on irregularly shaped objects and such a uniform coating would often be highly adavntageous.

It is an object of this invention to provide a non-electrolytic process for the plating of aluminum onto a substrate. An additional object is to provide a relatively low temperature process for the plating of aluminum from aluminum hydrides which permits the plating of heat sensitive substrates. Another object is to provide a process for coating predetermined portions of a substrate to provide designs, patterns or letters thereon. A further object is to provide a process whereby an irregularly shaped substrate is coated relatively uniformly with metallic aluminum. These and other objects and advantages of the present process will become apparent from a reading of the following detailed description.

It has now been discovered that, in contact with certain transition metal catalysts, aluminum hydrides may be used to produce plating of metallic aluminum at temperatures substantially below the usual decomposition temperature of such hydrides. The use of such catalysts permits the deposition of a uniform, adherent plate or coating of metallic aluminum, usually in the form of a bright plate, on substantially any substrate at relatively low temperatures and therefore provides the art with a novel and relatively inexpensive process for aluminum plating of even those materials, such as organic polymers, which are heat sensitive.

Substantially any normally solid material is suitable as a substrate herein. For example, metals such as iron, magnesium, brass and copper, polymers such as polyolefins, polyamides and polymeric fluorocarbons, glass, paper, cloth, carbon and graphite, wood, ceramics and the like are all plated with aluminum by the process of this invention. The nature of the surface being plated determines to a large extent the brightness of the aluminum plate. In general, the use of a smooth, non-porous surface such as found on most metals and some polymer films produces a brighter plate than a relatively porous surface such as those encountered with paper or cloth. On the surfaces of some polymers such as polyethylene, polytetrafluoroethylene, acrylonitrile-butadienestyrene terpolymers and polypropylene, it has been found that even better adhesion of the aluminum plate is achieved if the surface has been made more polar, e.g. by sulfonation, corona discharge and the like, prior to plating with the aluminum.

The term "aluminum hydride" is used herein in its broad sense and is meant to include anhydride compound which contains at least one aluminum atom to which at least one hydrogen atom is directly bonded and includes both the solvated and non-solvated forms of those aluminum hydrides occurring in both forms. Included, therefore, are aluminum trihydride, the substituted aluminum hydrides such as those having the empirical formula $AlH_nX_{3-n}$ wherein X is a halogen, an —OR group or an —R group (wherein R is an alkyl, substituted alkyl, aryl or substituted aryl group) and n has a numerical value equal to or less than 3. Also included are the complex aluminum hydrides such as $LiAlH_4$, $NaAlH_4$, $g(AlH_4)_2$ and the like and complex substituted aluminum hydrides such as those having the empirical formula $M(AlH_mX_{4-m})_a$ wherein X has the definition given above, m has a numeral value equal to or less than 4 and M is a metal or mixture of metals, preferably an alkali or alkaline earth metal and d has a numerical value equal to the valence of M. Of particular utility are the relatively simple aluminum hydrides containing at least two hydrogen atoms attached to the aluminium, e.g. $AlH_3$, $AlH_2Cl$, $AlH_2Br$, $LiAlH_4$, and the like. Mixtures of the various aluminum hydrides may also be employed.

It is usually desirable for ease of application to employ the aluminum hydride in solvated form. Compounds known to solvate or form complexes with the aluminum hydrides include ethers and other oxygen-containing organic compounds, and compounds containing a functional group such as a divalent sulfur atom, or trivalent nitrogen or trivalent phosphorous atom which is capable of allowing the solvation of an aluminum hydride with such compound. It is usually preferred that the solvate be an etherate and a wide variety of ethers containing from about 2 to about 20 carbon atoms are suitable. Usually the lower aliphatic ethers such as ethyl, propyl, or butyl ethers are employed but those containing an aromatic group such as methylphenyl ether, ethylphenyl ethers, propylphenyl ether or the alicyclic ethers such as tetrahydrofuran and the like may be employed.

In general, to achieve ease and uniformity of application, any solvent or mixture of solvents or suspending agents for the aluminum hydride may be employed which will not react with the aluminum hydride beyond the formation of a complex or solvate. Suitable solvents include aromatic hydrocarbons such as benzene, toluene and xylene, aliphatic hydrocarbons such as hexane, ethers, tertiary amines and the like.

If desired, such aluminum hydrides may be prepared in situ simultaneously with the plating step by employing aluminum hydride-forming reactants such as mixtures of lithium aluminum hydride and aluminum chloride, or sodium aluminum hydride and aluminum bromide, or the like. The presence of a metal halide such as LiCl, $MgCl_2$ or $AlCl_3$ together with the aluminum hydride is not detrimental to the plating reaction.

Due to the sensitivity of most aluminum hydrides to the presence of moist air, it is usually desirable that the application of the aluminum plate be conducted in a substantially anhydrous inert atmosphere.

In order to produce decomposition of the aluminum hydrides below their normal decomposition temperatures and to cause the aluminum thus produced to form a coating or plate on the substrate, it is necessary to contact the aluminum hydride with certain transition metal decomposition actalysts. Transition metal decomposition catalysts useful herein are compounds of the metals occurring in Groups IVb and Vb of the Periodic Table. In instances where the catalyst is applied to the substrate in a solvent, it is preferable that the metal be in the form of a compound which is soluble to the extent of at least $1\times10^{-6}$ weight percent of the solvent employed. For example, such compounds as $ZrCl_4$, $NbCl_5$, $VOCl_2$, $VOCl_3$, $TiCl_4\cdot2[(C_2H_5)_2O]$, $TiCl_4$, $TiBr_4$, $VCl_4$, $Ti(OC_2H_5)_2Cl_2$, $TiCl_2(i\text{-}OC_3H_7)_2$, $TiCl_2\cdot2[C_2H_5)_2O]$, $$Ti(BH_4)_3\cdot2[(C_2H_5)_2O]$$

have proved effective. Some of the transition metal catalysts defined herein have a more pronounced effect than others in lowering the decomposition temperature of the aluminum hydride. The chloride, bromides and oxychlorides of titanium, niobium, vanadium and zirconium generally seem to be more effective than the other compounds of Group IVb and Vb transition metals and $TiCl_4$ has been found particularly effective in achieveing lower temperature decomposition of the aluminum hydrides and plating of the aluminum thus produced. If the defined catalysts are not employed, undesirably high temperatures are required to produce decomposition of the aluminum hydride. At such elevated temperatures, even when decomposition is achieved, there is usually no aluminum coating or plate formed thereby.

The transition metal decomposition catalyst is preferably applied to the substrate prior to contact with the aluminum hydride. Such decomposition catalyst may be applied to the substrate directly as a finely divided solid, as a liquid solution or suspension or, where the nature of the catalyst and the substrate permit, deposited by vapor deposition. Preferably, however, the substrate is contacted with a sufficient quantity of a relatively dilute solution of the catalyst to wet the surface of the substrate. The solvent for the catalyst is then removed, e.g. by evaporation, leaving the catalyst substantially uniformly dispersed over the surface to be plated. Catalyst solutions at least about $1\times10^{-6}$ weight percent in decomposition catalyst, and preferably in concentrations of from about $5\times10^{-5}$ to about 100 weight percent of catalyst when applied to the substrate provide sufficient catalyst to achieve plating of aluminum for an aluminum hydride at a significantly lower temperature than is possible where no catalyst is employed. It has been found that uniformity of distribution of the catalyst on the substrate has a significant effect on both the uniformity and thickness of the aluminum plate. It is, therefore, desirable to apply the catalyst to the substrate in a manner which will assure relatively uniform distribution.

For substrates, such as magnesium metal and some polymers, having surface characteristics making uniform distribution of a catalyst solution or aluminum hydride difficult to achieve, it has been found advantageous to add to such solution a small amount, e.g. from about 0.0001 to about 5.0 weight percent, of a wetting agent. Suitable wetting agents include, for example, stearates such as sodium or aluminum stearate or aluminum alkoxides such as aluminum isopropoxide.

Solvents for the transition metal decomposition catalysts are those normally liquid materials in which the catalyst is soluble to at least the extent of $1\times16^{-6}$ weight percent, which will not adversely affect the substrate and which will not change the anion of the catalyst sufficiently to render it insoluble. Suitable solvents include nonreactive solvents such as benzene, hexane, and halogenated hydrocarbons, reactive solvents such as alcohols, aldehydes, ketones, mercaptans, carboxylic acids and mineral acids, and coordinating solvents such as ethers, nitriles, amides and amines.

By application of the transition metal decomposition catalyst to only selected areas of the substrate, it is possible to form an aluminum plate only on such selected areas. In this manner, ornamental designs, outlines, printed circuits and the like may be produced. Likewise, all or a portion of a selected substrate may be coated or plated with aluminum to enhance the ability of such surface to adhere to other materials. Of particular utility is the aluminum coating of glass, ceramic, metal or polymer surfaces to enhance their bonding to adhesive polymers and copolymers such as the copolymers of ethylene and acrylic acid.

Once the desired form and quantity of decomposition catalyst is applied to the substrate, the catalyzed substrate surface is contacted with a suitable form of aluminum hydride. In general, it is desirable to apply the aluminum hydride as a solution or suspension containing at least $1\times10^{-4}$ weight percent, preferably from 0.1 molar to 1.0 molar or more, aluminum hydride which may be applied by dipping, spraying or other suitable means. However, good results are also achieved by contacting the catalyzed substrate surface with a finely divided solid aluminum hydride. Alternatively, a vapor phase deposition of aluminum may be achieved at below usual decomposition temperatures by heating an aluminum hydride in close proximity to a catalyzed substrate surface. With or without the use of reduced pressure, a coating of metallic aluminum will form on the catalyzed surface.

In some applications, such as plating a vertical surface, it is desirable to increase the viscosity of either the catalyst solution or the aluminum hydride solution or both. Such increase in viscosity may be achieved with known gelling or thickening agents such as aluminum octanoate or mineral oils without adversely affecting the plating reaction.

Most of the catalysts defined herein will produce plating from the aluminum hydride at room temperature in a period of time from a few minutes to a few hours. More rapid decomposition of the catalyzed aluminum hydride to cause plating of the aluminum on a substrate may be achieved, however, by the application of sufficient energy thereto to initiate the deposition. For example, the aluminum hydride and catalyst may be applied to a substrate which is heated to the required temperature, or a catalyzed substrate may be contacted with a heated bath containing aluminum hydride. Alternatively, actinic light such as cold ultraviolet light may be employed or high energy radiation such as electron bombardment may be used to produce relatively rapid aluminum plating at low temperatures, e.g. room temperature. Likewise, combinations of such forms of energy may be used. In general, once the decomposition of the catlyzed aluminum hydride is initiated, it will be self-sustaining and will form a continuous plate without supplying additional energy.

The deposition temperature of aluminum catalyzed by the transition metal catalysts defined herein will vary depending on the particular aluminum hydride employed, upon the catalyst used, to some extent, upon the catalyst concentration and upon the type of energy used to initiate the decomposition of the aluminum hydride. Such deposition temperatures wil, however, be substantially lower than those required where no catalyst is present.

The following examples are provided to further illustrate the invention but are not to be construed as limiting the scope thereof.

Example 1

An aluminum hydride solution was prepared in a dry nitrogen atmosphere by admixing 49 ml. of 1.0 molar lithium aluminum hydride, 18.5 ml. of 0.98 molar aluminum chloride and 156 ml. of diethyl ether. After stirring, the solution was decanted to produce a 0.3 molar solution of aluminum hydride in diethyl ether.

Various substrates were immersed in a 0.046 molar solution of $TiCl_4$ in diethyl ether, dried at 100° C., cooled to room temperature, immersed in the aluminum hydride solution prepared above and again dried at room temperature. Within a few minutes, a uniform, adherent aluminum coating was deposited on all surfaces of the substrate which had come in contact with the catalyst solution. The following table shows the substrates employed and type of coat obtained:

TABLE I

| Substrate: | Appearance of aluminum coat |
|---|---|
| Polyamide film (Mylar) | Mirror |
| Cellophane film | Mirror |
| Saran film | Mirror |
| Polyethylene film (surface treated by electric discharge) | Mirror |
| Glass plate | Mirror |
| Fiberglass cloth | Shiny |
| Polyvinyl chloride film | Mirror |
| Porous paper sheet | Dull |
| Brass strip | Mirror |

Example 2

In a manner similar to that of Example 1, a 0.3 molar solution of aluminum hydride in ether was prepared and several strips of Mylar film were coated with $TiCl_4$ in hexane and dried. To this solution were added 3 cc. increments of a 1.2 molar $AlCl_3$ solution in diethyl ether. After each addition, one of the above catalyzed Mylar strips was immersed in the aluminum hydride solution. Upon exposure to an ultraviolet sun lamp, decorative, aluminum film was deposited on the film. Each film was evaluated as to the effect of excess $AlCl_3$ on the decorative nature of the plate.

It was found that a decorative plate could be obtained from solutions containing up to about 50-50 weight ratio of $AlCl_3$ to $AlH_3$. Some dark colored background streaking was noted on plates formed from solutions containing higher $AlCl_3$ concentrations.

Example 3

In a manner similar to that of Example 2, strips of Mylar, Saran, polyethylene and glass were dipped into a 0.046 molar solution of $TiCl_4$ in benzene. The catalyzed films were then dried and immersed in an 0.30 molar aluminum hydride solution in ether. After removal from the ether solution, the substrates were placed in a convective oven heated to 110° C. A mirror-like, uniform, adhesive coating of aluminum was produced in from 2 to 3 seconds.

As controls, substrates of the same materials not treated with $TiCl_4$ were immersed in the 0.3 molar aluminum hydride solution and also placed in the convective furnace. The furnace was slowly heated from 110° C. to 250° C. over a period of one hour. The organic substrates melted and gave no evidence of aluminum deposition on their surfaces. The glass substrate showed no evidence of aluminum deposition even at 250° C.

Example 4

In a dry nitrogen atmosphere, two strips of Mylar having a thickness of 0.002 inch were immersed in a 0.046 molar solution of $TiCl_4$ in diethyl ether, dried at room temperature, immersed in a diethyl ether solution of 0.266 molar solution in aluminum hydride and 0.005 molar in aluminum isopropoxide. The films were dried at room temperature and one film was exposed at ambient temperature to one megarad of high energy electron flow. A mirror-like aluminum plate was formed extremely rapidly on this substrate.

The second strip of Mylar film, used as control, and not exposed to ionizing radiation, showed no aluminum plating in the same time interval.

Example 5

In a manner similar to that of Example 1, a strip of Mylar film having a thickness of 0.002 inch was immersed into a 0.05 molar solution niobium pentachloride ($NbCl_5$) in diethyl ether for about 5 seconds, dried, immersed in a diethyl ether solution 0.3 molar in aluminum hydride and about 0.005 molar in aluminum isopropoxide for about 5 seconds and dried again. The treated film was then heated to about 80° C. A uniform aluminum coating having a mirror-like appearance was almost immediately formed on the Mylar film.

In the same manner, an aluminum plating was formed on Mylar film by immersing the film in a 0.05 molar solution of zirconium tetrachloride in diethyl ether, drying the treated film, immersing the film in the aluminum hydride solution as above, drying the film and heating to a temperature of 80° C.

In the same manner, an aluminum plate was formed at 80° C. on Mylar film employing a 0.03 molar solution of titanium tetrabromide as the catalyst solution.

In the same manner, an aluminum plate was formed at 110° C. on Mylar film employing a 0.05 molar solution of vanadium oxydichloride ($VOCl_2$) in diethyl ether as the catalyst solution.

Example 6

A strip of Mylar was coated with a thin layer of $TiCl_4$ by exposing it to vapors of $TiCl_4$. Immersion of the film thus treated in 0.2 molar aluminum hydride solution and subsequent heating of the film to 80° C. with infrared light yielded a shiny, adherent aluminum plate.

In a related experiment, solid $TiOCl_2$ was suspended in mineral oil and applied to one side of an 0.002 inch thick Mylar film by brushing. Immersion of the film in 0.2 molar aluminum hydride solution in diethyl ether followed by exposure to infrared light yielded a mirror-like aluminum plate on the side of the film to which the catalyst had been applied. The uncatalyzed surface of the film was not plated with aluminum.

In a similar manner, solid $TiCl_4 \cdot 2[(C_2H_5)_2O]$ suspended in mineral oil and applied with a brush to a Mylar film also gave a mirror plate only on the catalyzed surface of the film.

Example 7

A design was drawn on a strip of Mylar film with a glass rod dipped in a 0.046 molar solution of $TiCl_4$ in benzene. After evaporation of the benzene, the film was immersed in a diethyl ether solution 0.2 molar in aluminum hydride and 0.001 molar in aluminum isopropoxide. The film was then removed from the ether solution and heated to about 80° C. under an infrared lamp for 2 minutes. At the end of this time, aluminum was found to have plated only the area of the design originally made with the $TiCl_4$ solution.

In a similar manner, another portion of the above catalyst solution was transferred to a Plexiglas surface with a rubber stamp. Upon immersion in an 0.3 molar aluminum hydride ether solution and exposure to infrared light, the printed statement contained on the original rubber stamp was rapidly formed on the Plexiglas surface in the form of shiny, adherent aluminum letters.

In a related experiment a suspension of $$TiCl_4 \cdot 2[(C_2H_5)_2O]$$

in mineral oil was applied with a brush to a cardboard stencil over a Mylar surface. Treatment as described above yielded a lettered design of metallic aluminum on the substrate.

lowing table shows the solvents and concentrations employed and the results obtained.

TABLE II

| Substrate | Molar Conc., $AlH_3$ | Solvent used for catalyst | Conc., $TiCl_4$,M | Method used to develop plate | Approximate temperature of substrate (C.) | Type of coating |
|---|---|---|---|---|---|---|
| Mylar | 0.2 | Ether | 0.00018 | Infrared lamp | 80 | Mirror finish. |
| Do | 0.3 | Ethanol | 0.90 | do | 80 | Do. |
| Do | 0.3 | Isopropanol | 0.90 | do | 80 | Do. |
| Do | 0.3 | Carbon tertrachloride | 0.90 | do | 80 | Do. |
| Do | 0.3 | Methylene chloride | 0.90 | do | 80 | Do. |
| Polypropylene (sulfonated) | 0.25 | Heptane | 0.045 | Convective furnace | 60 | Do. |
| Acrylonitriel-butadiene-styrene terpolymer. | 0.30 | Hexane | 0.045 | Infrared lamp | 80 | Dull. |
| Teflon (treated with sodium diphenyl). | 0.20 | Ether | 0.046 | U.V. lamp | 80 | Less shiny. |
| Wood | 0.25 | do | 0.046 | do | 80 | Dull. |
| Cottou | [1] 0.20 | Benzene | 0.0023 | do | 80 | Do. |
| Nylon | [1] 0.20 | do | 0.0023 | do | 80 | Less shiny. |
| Animal hair | 0.40 | do | 0.046 | do | 80 | Dull. |

[1] 0.005 M in aluminum isopropoxide.

Example 8

In a manner similar to that of Example 3, a strip of Mylar film having a thickness of 0.002 inch was immersed in a 0.3 molar aluminum hydride solution. The film was dried at approximately 80° C. and then immersed in a 0.045 molar solution of $TiCl_4$ in benzene. Upon heating the above treated film to about 80° C. a mirror-like aluminum plate was formed on the substrate.

Similar experiments were conducted wherein the $TiCl_4$ was added to the aluminum hydride solution. An aluminum plate was obtained on a Mylar film which had been dipped into the mixture of catalyst and aluminum hydride.

In each of the above experiments, controls containing no catalyst produced no aluminum plating.

Example 9

In a dry nitrogen atmosphere, a strip of Mylar film 0.002 inch in thickness was dipped into a 0.046 molar solution of $TiCl_4$ in n-hexane. The treated strip of film was dried under an infrared heat lamp and then dipped into a 0.3 molar solution of aluminum dihydride isopropoxide $[AlH_2(i—OC_3H_7)]$, in diethyl ether. The film was held under an infrared heat lamp for several minutes to produce a temperature of about 80° C. on the surface of the substrate. A uniform coating of aluminum was obtained on the Mylar.

In a similar manner, uniform aluminum coatings were obtained on strips of Mylar from a 0.3 molar diethyl ether solution of isobutyl aluminum dihydride $$[AlH_2(i—C_4H_9)]$$

a 0.25 molar diethyl ether solution of $LiAlH_4$, a 0.2 molar benzene solution of aluminum trihydride trimethyl amine adduct $[AlH_3 \cdot N(CH_3)_3]$, and a 0.4 molar solution of $AlH_2Cl \cdot 2$ tetrahydrofuranate.

Example 10

In a dry nitrogen atmosphere, a strip of Mylar film was immersed in a 0.046 molar solution of $TiCl_4$ in benzene and dried at about 80° C. A glass microscope slide was immersed in an 0.3 molar solution of aluminum hydride in diethyl ether. The catalyzed Mylar film was then supported 0.006 inch above the aluminum hydride coated glass slide and the slide was placed on a hot plate. The hot plate was then heated to 150° C. a continuous shiny coating of aluminum was obtained on the catalyzed Mylar film.

A duplicate experiment was conducted except that the Mylar film was not catalyzed with $TiCl_4$. No aluminum was deposited on the uncatalyzed Mylar film.

Example 11

In a nitrogen filled dry box strips of various substrates were immersed in a solution of $TiCl_4$ for about 1 second, dried, immersed in a solution of aluminum hydride in ether and then dried under various conditions. The fol-

Example 12

In a nitrogen filled dry box a strip of sanded magnesium metal was immersed in a benzene solution 0.4 molar in $TiCl_4$ for approximately 30–60 seconds. The above solution contained about 0.006 weight percent of sodium stearate. The catalyzed magnesium strip was dried, dipped in an 0.4 molar solution of aluminum hydride in diethyl ether and briefly dried on a hot plate at 150° C. A light coat of metallic aluminum was deposited on the treated magnesium surface in a few seconds.

As a control, a duplicate sample of sanded magnesium metal was treated in an identical manner except it was not contacted with the $TiCl_4$ catalyst. No coat of aluminum was formed thereon in the same time period at 150° C.

Example 13

In a dry nitrogen atmosphere, a strip of Mylar film was immersed in a 0.9 molar solution of $TiCl_4$ in hexane to which 20 volume percent mineral oil had been added to increase the viscosity. This catalyst solution, due to its viscosity, deposited a heavier concentration of catalyst on the substrate than the less viscous catalyst solutions. The treated film was dried, immersed in a 0.3 molar solution of aluminum hydride in diethyl ether and heated to 80° C. An unusually heavy mirror coating of aluminum was produced on the surface of the substrate.

Example 14

A strip of Mylar film was immersed in a 0.046 molar solution of $TiCl_4$ in diethyl ether and dried. The catalyzed surface of the film was dusted with a fine powder of solid aluminum trihydride etherate and then heated to about 80° C. with an infrared lamp. A mirror-like adherent coat of metallic aluminum was substantially uniformly deposited on the catalyzed surface of the film.

Various modifications can be made in the present invention without departing from the spirit or scope thereof for it is understood that we limit ourselves only as defined in the appended claims.

We claim:

1. A process for the plating of aluminum from an aluminum hydride onto a substrate which comprises: *sequentially* contacting *a substrate with* [an aluminum hydride and] a decomposition catalyst *and then an aluminum hydride, said hydride and catalyst being* in the presence of each other [, with a substrate] for a time sufficient to deposit metallic aluminum onto said substrate, said decomposition catalyst being selected from the group consisting of compounds of the metals of Groups IVb and Vb of the Periodic Table and mixtures thereof.

2. The process of claim 1 wherein the catalyzed aluminum hydride in contact with the substrate is subjected to at least sufficient energy to initiate the deposition of the aluminum plate.

3. The process of claim 1 wherein the aluminum hydride is a substituted aluminum hydride.

4. The process of claim 3 wherein the substituted aluminum hydride contains two hydrogen atoms bonded directly to the aluminum.

5. The process of claim 1 wherein the aluminum hydroxide is a complex aluminum hydride.

6. The process of claim 1 wherein the aluminum hydride is $LiAlH_4$.

7. The process of claim 1 wherein the aluminum hydride is a solvated aluminum trihydride.

8. The process of claim 1 wherein the aluminum hydride is a compound having the empirical formula of a solvated aluminum chlorodihydride.

9. The process of claim 1 wherein the decomposition catalyst is a member selected from the group consisting of $ZrCl_4$, $NbCl_5$, $VOCl_2$, $VOCl_3$, $TiCl_4 \cdot 2[(C_2H_5)_2O]$, $TiCl_4$, $TiBr_4$, $VCl_4$, $Ti(OC_2H_5)_2Cl_2$, $TiCl_2(i\text{-}OC_3H_7)_2$, $TiCl_2 \cdot 2[(C_2H_5)_2O]$, $Ti(BH_4)_3 \cdot 2[(C_2H_5)_2O]$ and mixtures thereof.

10. The process of claim 1 wherein the decomposition catalyst is $TiCl_4$.

11. The process of claim 2 wherein the energy to initiate the deposition of metallic aluminum from the catalyzed aluminum hydride is heat.

12. The process of claim 2 wherein the energy to initiate deposition of metallic aluminum from the catalyzed aluminum hydride is actinic light.

13. The process of claim 2 wherein the energy to initiate deposition of metallic aluminum from the catalyzed aluminum hydride is high energy radiation.

14. The process of claim 1 wherein the decomposition catalyst is applied to the substrate as a solution containing at least $1 \times 10^{-6}$ weight percent catalyst and the aluminum hydride is applied to the catalyst-treated substrate as a solution containing at least 0.0001 weight percent aluminum hydride.

15. The process of claim 1 wherein the substrate is a heat sensitive polymer.

16. The process of claim 1 wherein the catalyst is applied to only a portion of the substrate to thereby produce a metallic aluminum design.

17. A process for the plating of aluminum from an aluminum hydride onto a substrate which comprises applying to a substrate a decomposition catalyst selected from the compounds of the metals of Groups IVb and Vb of the Periodic Table and mixtures thereof subsequently contacting the catalyst-containing substrate with a solution of an aluminum hydride and maintaining contact between the aluminum hydride and the catalyst-containing substrate for a period sufficient to deposit metallic aluminum thereon.

18. The process of claim 17 wherein the aluminum [is subjected to at least sufficient energy to initiate the] hydride in contact with the catalyst-treated substrate *is subjected to at least sufficient energy to initiate the* deposition of the aluminum from the aluminum hydride.

19. The process of claim 17 wherein the decomposition catalyst is a member selected from the group consisting of $ZrCl_4$, $NbCl_5$, $VOCl_2$, $VOCl_3$, $TiCl_4 \cdot 2[(C_2H_5)_2O]$, $TiCl_4$, $TiBr_4$, $VCl_4$, $Ti(OC_2H_5)_2Cl_2$, $TiCl_2(i\text{-}OC_3H_7)_2$, $TiCl_4 \cdot 2[(C_2H_5)_2O]$, $Ti(BH_4)_3 \cdot 2[(C_2H_5)_2O]$ and mixtures thereof.

20. The process of claim 17 wherein the catalyst is $TiCl_4$.

21. The process of claim 17 wherein the catalyst is applied to the substrate as a solution containing at least $5 \times 10^{-5}$ weight percent catalyst.

22. The process of claim 17 wherein the aluminum hydride is a substituted aluminum hydride.

23. The process of claim 22 wherein the substituted aluminum hydride contains two hydrogen atoms bonded directly to the aluminum.

24. The process of claim 17 wherein the aluminum hydride is solvated aluminum trihydride.

25. The process of claim 17 wherein the aluminum hydride is a compound having the empirical formula of a solvated chlorohydride.

26. The process of claim 17 wherein the aluminum hydride is a complex aluminum hydride.

27. The process of claim 17 wherein the aluminum hydride is $LiAlH_4$.

28. The process of claim 17 wherein the aluminum hydride is applied as a solution in an ether containing at least $1 \times 10^{-4}$ weight percent of the aluminum hydride.

29. The process of claim 18 wherein the energy to initiate the deposition of metallic aluminum from the catalyzed aluminum hydride is heat.

30. The process of claim 18 wherein the energy to initiate the deposition of metallic aluminum from the catalyzed aluminum hydride is actinic light.

31. The process of claim 18 wherein the energy to initiate deposition of metallic aluminum from the catalyzed aluminum hydride is high energy radiation.

32. The process of claim 17 wherein the substrate is a heat sensitive polymer.

33. The process of claim 17 wherein the catalyst is applied only to a portion of the substrate to produce a metallic aluminum design.

34. The process of claim 17 wherein the aluminum hydride is applied to the substrate as a suspension.

35. A process for the plating of aluminum from an aluminum hydride onto a substrate which comprises (a) contacting a substrate with a solution containing at least $1 \times 10^{-6}$ weight percent of a catalyst selected from the group consisting of compounds of the metals of Groups IVb and Vb of the Periodic Table and mixtures thereof, (b) removing the solvent in a manner to leave the catalyst in contact with the substrate [.], (c) contacting the catalyst-containing substrate with a solution containing at least $1 \times 10^{-4}$ weight percent of an aluminum hydride, and (d) applying at least sufficient energy to initiate deposition of metallic aluminum from the aluminum hydride.

36. The process of claim 35 wherein the aluminum hydride is a substituted aluminum hydride.

37. The process of claim 36 wherein the substituted aluminum hydride contains two hydrogen atoms bonded directly to the aluminum.

38. The process of claim 35 wherein the aluminum hydride is a solvated aluminum trihydride.

39. The process of claim 35 wherein the aluminum hydride is a compound having the empirical formula of a solvated aluminum chlorodihydride.

40. The process of claim 35 wherein the aluminum hydride is a complex aluminum hydride.

41. The process of claim 35 wherein the aluminum hydride is $LiAlH_4$.

42. The process of claim 35 wherein the decomposition catalyst is a member selected from the group consisting of $ZrCl_4$, $NbCl_5$, $VOCl_2$, $VOCl_3$, $TiCl_4 \cdot 2[(C_2H_5)_2O]$, $TiCl_4$, $TiBr_4$, $VCl_4$, $Ti(OC_2H_5)_2Cl_2$, $TiCl_2(i\text{-}OC_3H_7)_2$, $TiCl_2 \cdot 2[(C_2H_5)_2O]$, $Ti(BH_4)_3 \cdot 2[(C_2H_5)_2O]$ and mixtures thereof.

43. The process of claim 35 wherein the decomposition catalyst is $TiCl_4$.

44. The process of claim 35 wherein the energy to initiate the deposition of metallic aluminum from the catalyzed aluminum hydride is heat.

45. The process of claim 35 wherein the energy to initiate the deposition of metallic aluminum from the catalyzed aluminum hydride is actinic light.

46. The process of claim 35 wherein the energy to initiate the deposition of metallic aluminum from the catalyzed aluminum hydride is high energy radiation.

47. The process of claim 35 wherein the substrate is a heat sensitive polymer.

48. The process of claim 35 wherein the catalyst solution is applied to only a portion of the substrate to thereby produce a metallic aluminum design.

49. The process of claim 35 wherein from about 0.0001 to about 5 weight percent of a wetting agent is contained in either the catalyst solution or the aluminum hydride solution.

50. The process of claim 49 wherein the wetting agent is an aluminum alkoxide.

51. The process of claim 49 wherein the wetting agent is aluminum isopropoxide.

52. The process of claim 49 wherein the wetting agent is sodium stearate.

53. The process of claim 49 wherein the wetting agent is aluminum stearate.

*54. The process of claim 1 wherein the hydride and catalyst contacted substrate is subjected to a temperature range of from room temperature to 150° C.*

*55. The process of claim 54 wherein the aluminum hydride contains at least 2 hydrogen atoms attached to the aluminum.*

*56. The process of claim 1 wherein said decomposition catalyst is selected from the group consisting of chlorides, bromides and oxychlorides of titanium, niobium, vanadium and zirconium.*

References Cited

The following references, cited by the Examiner, are of record in the patented file of this patent or the original patent.

UNITED STATES PATENTS

| | | | |
|---|---|---|---|
| 3,206,326 | 9/1965 | Whaley et al. | 117—107.2 |
| 3,449,144 | 6/1969 | Williams et al. | 117—6 |

FOREIGN PATENTS

| | | |
|---|---|---|
| 915,385 | 1/1963 | Great Britain. |

OTHER REFERENCES

Japanese Patent Publication 9660/1964, June 5, 1964, Kiyoshi Toshima et al.

Japanese Patent Publication 1318/1964, Feb. 12, 1964, Thomas Patrick Whaley et al.

Japanese Patent Publication 2454/1957, Apr. 22, 1957, Gerlert et al.

RALPH S. KENDALL, Primary Examiner

U.S. Cl. X.R.

117—38, 47 R, 93.3, 107.2, 130, 138.8 R, 160 R